(12) United States Patent
Pandya et al.

(10) Patent No.: US 12,102,624 B2
(45) Date of Patent: Oct. 1, 2024

(54) PANTOPRAZOLE COMPOSITIONS AND METHODS

(71) Applicant: NIVAGEN PHARMACEUTICALS, INC., Sacramento, CA (US)

(72) Inventors: Brijeshkumar B. Pandya, Sacramento, CA (US); Govind R. Jagadale, Sacramento, CA (US); Dasaradhi Lakkaraju, Sacramento, CA (US); Bala Tripura Sundari Chodavarapu, Davis, CA (US); Anand Shukla, Denver, CO (US); Jwalant Shukla, Sacramento, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 442 days.

(21) Appl. No.: 17/446,063

(22) Filed: Aug. 26, 2021

(65) Prior Publication Data

US 2022/0062253 A1    Mar. 3, 2022

Related U.S. Application Data

(60) Provisional application No. 63/070,510, filed on Aug. 26, 2020.

(51) Int. Cl.
*A61K 31/4439* (2006.01)
*A61J 1/10* (2006.01)
*A61K 9/16* (2006.01)

(52) U.S. Cl.
CPC ............. *A61K 31/4439* (2013.01); *A61J 1/10* (2013.01); *A61K 9/1611* (2013.01); *A61K 9/1694* (2013.01)

(58) Field of Classification Search
CPC . A61K 31/4439; A61K 9/1611; A61K 9/1694
See application file for complete search history.

(56) References Cited

U.S. PATENT DOCUMENTS

| 2003/0003058 | A1  | 1/2003  | Linder et al. |
| 2003/0203036 | A1* | 10/2003 | Gordon ............... A61K 31/353 514/682 |
| 2006/0240100 | A1  | 10/2006 | Anstett |
| 2008/0139623 | A1* | 6/2008  | Hedvati .................... A61P 1/00 546/273.7 |

FOREIGN PATENT DOCUMENTS

| CA | 2930072 A1 * | 12/2008 | ............... A61J 1/00 |
| CN | 101229138 A  | 7/2008  | |
| CN | 102743351 A  | 10/2012 | |
| CN | 103202816 A  | 7/2013  | |
| WO | WO-2004056804 A2 * | 7/2004 | ........... C07D 401/12 |
| WO | WO-2007014928 A1 * | 2/2007 | ......... A61K 31/4439 |
| WO | WO-2017012935 A1 * | 1/2017 | ............. A61K 31/18 |

OTHER PUBLICATIONS

Baheti et al., "Excipients used in lyophilization of small molecules," J. Excipients and Food Chem., 2010; 1(1):41-54.

* cited by examiner

*Primary Examiner* — Sarah Pihonak
*Assistant Examiner* — Mikhail O'Donnel Robinson
(74) *Attorney, Agent, or Firm* — Umberg Zipser LLP

(57) ABSTRACT

A spray-dried storage stable pantoprazole composition is provided. The pantoprazole composition includes a pantoprazole and an excipient matrix including sodium chloride (NaCl). The pantoprazole is substantially uniformly dispersed in the excipient matrix. A method for forming a storage stable pantoprazole composition is also provided. The method includes combining a bulking agent and water to form a first solution, combining a pantoprazole and the first solution to form a second solution, combining sodium hydroxide and the second solution to form a bulk solution, and removing water from the bulk solution by drying to form the storage stable pantoprazole composition.

20 Claims, 4 Drawing Sheets

PANTOPRAZOLE COMPOSITIONS AND METHODS

CROSS-REFERENCE TO RELATED APPLICATIONS

This application is U.S. Non-provisional Patent Application which claims priority to U.S. Provisional Patent Application No. 63/070,510, filed Aug. 26, 2020, which is hereby incorporated in its entirety by reference.

FIELD OF THE INVENTION

The field of the invention is a ready-to-use (RTU) pantoprazole sodium composition for injection, and especially a stable composition in an easy-to-use system for administration.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Pantoprazole is a medication used for the treatment of stomach ulcers, short-term treatment of erosive esophagitis due to gastroesophageal reflux disease (GERD), maintenance of healing of erosive esophagitis, and pathological hypersecretory conditions including Zollinger-Ellison syndrome. It may also be used along with other medications to eliminate *Helicobacter pylori*. Effectiveness is similar to other proton pump inhibitors (PPIs). It is available as a solid for oral administration and as an injectable for intravenous (I.V.) administration.

The stability of the pantoprazole compound in aqueous solution is pH-dependent with the rate of degradation increasing with decreasing pH. The reconstituted solution of PROTONIX I.V. for injection (Wyeth Pharmaceuticals LLC) is in the pH range 9.0 to 10.5. PROTONIX I.V. is supplied for intravenous administration as a sterile, freeze-dried powder in a single-dose clear glass vial fitted with a rubber stopper and crimp seal. Each vial contains 40 mg pantoprazole (equivalent to 45.1 mg of pantoprazole sodium), edetate disodium (1 mg), and sodium hydroxide to adjust pH.

The reconstituted solution of Pantoprazole Sodium for Injection is in the pH range 9.5 to 11.5. Pantoprazole Sodium for injection (Hikma Pharmaceuticals LLC) is supplied for intravenous administration as a sterile lyophilized powder in a single-dose clear glass vial fitted with a rubber stopper and crimp seal. Each vial contains 40 mg pantoprazole (equivalent to 45.1 mg of pantoprazole sodium), and sodium hydroxide to adjust pH.

However, storage of the pantoprazole powder in glass vials exposes the pantoprazole sodium to light which increases degradation of the composition. Furthermore, the preparation of an injectable solution using a stoppered glass vial is often contaminated, making the preparation of an aseptic intravenous solution of pantoprazole sodium time consuming and costly.

Solutions of pantoprazole including saline solution have been refrigerated for up to 28 days at 2° C. to 8° C. See, e.g., Donnelly, 2011, *Can J Hosp Pharm.* 2011 May; 64(3): 192-8. However, refrigeration is not always available or practical and the solutions still suffer from inaccurate dosing due to the use of conventional reconstituted pantoprazole sodium for injection (Sandoz Canada Inc, Boucherville, Quebec).

Furthermore, because pantoprazole is hydrolytically labile, it must be lyophilized to ensure shelf-life stability. Considering the lower (e.g., milligrams) amounts of pantoprazole in a single dosage (e.g., 40 mg or 80 mg), additional excipients (e.g., bulking agents) are necessary to render the lyophilization process effective. See, e.g., Baheti et al., 2010, *J. Excipients and Food Chem.*, 1: 41-54. The pantoprazole active ingredient must remain sterile and homogenous for safe and effective administration to the patient; however, selection of bulking agents and lyophilization processes can impart increased variability and cost.

Thus, there is still a need for a ready-to-use (RTU) sterile pantoprazole powder that is stably stored and easily reconstituted while maintaining sterility to form an aseptic intravenous pantoprazole sodium preparation that can be cost effectively manufactured.

SUMMARY OF THE INVENTION

The inventors have advantageously contemplated a composition of a stabilized pantoprazole sodium blend made of pantoprazole present at 40 mg or 80 mg or a batch multiple thereof and a bulking agent, wherein the stabilized pantoprazole blend is a spray dried powder blend having no more than 0.20% pantoprazole sulfone degradant.

The contemplated bulking agent in the stabilized pantoprazole sodium blend may be a salt, an amino acid, a sugar, or a combination thereof. More specifically, the salt may be selected from sodium chloride (NaCl), magnesium chloride ($MgCl_2$), or calcium chloride ($CaCl_2$)), the amino acid may be glycine, and the sugar may be dextrose, sucrose, or trehalose. Preferably the bulking agent is NaCl. More preferably, the bulking agent is NaCl present at about 800 mg to 1 gram for each 40 mg or 80 mg dose of the pantoprazole. Most preferably, the bulking agent is NaCl at about 900 mg for each 40 mg or 80 mg dose of the pantoprazole.

The contemplated stabilized pantoprazole sodium blend composition may include NaOH at about 3 to 4 mg for each 40 mg or 80 mg dose of the pantoprazole.

In preferred embodiments, the stabilized pantoprazole sodium blend has no more than 0.30% pantoprazole sulfone degradant at a storage temperature up to about 25° C. In more preferred embodiments, the stabilized pantoprazole sodium blend has no more than 0.20% pantoprazole sulfone degradant at a storage temperature up to about 25° C.

In some embodiments, the contemplated method of making a stabilized pantoprazole sodium blend powder as disclosed includes deionized water. Preferably, the water is at a volume of about 80 ml for each 40 mg or 80 mg dose of the pantoprazole.

In further embodiments, the bulking agent added in the method of making the stabilized pantoprazole sodium blend powder is a salt, an amino acid, a sugar, or combination thereof. Preferably the salt is sodium chloride (NaCl), magnesium chloride (MgCl2), or calcium chloride (CaCl2); the amino acid is glycine; and the sugar is dextrose, sucrose, or trehalose. In more preferred embodiments, the bulking agent is NaCl. Most preferably, 900 mg of NaCl is added for each 40 mg or 80 mg dose of the pantoprazole to the first solution as disclosed.

In still further embodiments, the azeotropic agent added in the method of making the stabilized pantoprazole sodium blend powder is acetonitrile solution. Preferably, about 40 to 60 ml of acetonitrile solution are added for each 40 mg or 80 mg dose of the pantoprazole to the third solution as disclosed herein.

In additional embodiments, the third solution is filtered prior to the addition of the azeotropic agent.

In still other embodiments, the spray drying step of the contemplated method includes a set of parameters that are implemented in the spray drying process by the spray dryer, wherein the set of parameters include an inlet temperature of 120 to 220° C., an outlet temperature of 60 to 90° C., a flow rate of about 30 to 65 mm, and a feed rate of about 20 to 40%. Preferably, the set of parameters that are implemented in the spray drying process by the spray dryer include an inlet temperature of 145 to 180° C., an outlet temperature of 86 to 89° C., a flow rate of about 65 mm, and a feed rate of about 20 to 40%.

Notably, the inventors have contemplated a method of making a ready-to-use (RTU) pantoprazole sodium for injection in which the disclosed method of making the stabilized pantoprazole sodium blend powder additionally includes aseptically providing the stabilized pantoprazole sodium blend powder to a first pouch of a flexible container and sealing the first pouch with the stabilized pantoprazole sodium blend powder therein, and aseptically providing sterile water to a second pouch of the flexible container and sealing the second pouch with the sterile water therein, wherein the flexible container comprises the first and second pouches as two sealable compartments adjacent to each other having a frangible seal therebetween. Preferably, the sealing of the first and second pouchs is carried in the presence of nitrogen gas. Also, the flexible container is preferably made of or includes aluminum.

Considered from a different perspective, the inventors have also contemplated a system for forming and administering a ready-to-use (RTU) pantoprazole sodium solution for injection, in which the system includes a flexible container having two sealed compartments including a first pouch and a second pouch, wherein the two sealed compartments are adjacent to each other having a frangible seal therebetween. In this flexible container system, the stabilized pantoprazole sodium blend powder composition as disclosed herein is provided and sealed within the first pouch, and sterile water is provided and sealed within the second pouch, wherein the stabilized pantoprazole sodium blend powder has no more than 0.20% pantoprazole sulfone degradant. As disclosed herein, the stabilized pantoprazole sodium blend powder composition includes pantoprazole, sodium hydroxide, and a bulking agent.

In additional embodiments, the flexible container of the disclosed system has a vertical orientation in which the first pouch is aligned beneath the second pouch with the frangible seal forming both a topmost side of the first pouch and a bottommost side of the second pouch.

In preferred embodiments, 40 mg or 80 mg of the pantoprazole is present in the ready-to-use (RTU) pantoprazole sodium solution for injection. In other preferred embodiments, the sodium hydroxide is present in an amount of about 2 to 5 mg. More preferably, the sodium hydroxide is present in an amount of about 3 to 4 mg.

In still other embodiments, the bulking agent in the stabilized pantoprazole sodium blend powder composition of the contemplated system is a salt, an amino acid, a sugar, or a combination thereof. Preferably the salt is sodium chloride (NaCl), magnesium chloride ($MgCl_2$), or calcium chloride ($CaCl_2$)); the amino acid is glycine; and the sugar is dextrose, sucrose, or trehalose. In more preferred embodiments, the bulking agent in the stabilized pantoprazole sodium blend powder composition of the contemplated system is NaCl. Most preferably, NaCl is present at about 900 mg.

In additional embodiments, the flexible container of the contemplated system includes or is made of aluminum. The first pouch of the flexible container may be or may be made from an opaque material. The second pouch may include a transparent material.

In some embodiments, the forming of the RTU pantoprazole sodium solution includes breaking the frangible seal between the first pouch and the second pouch, thereby allowing the sterile water to combine with the stabilized pantoprazole sodium blend powder in the first pouch to thereby form the RTU pantoprazole sodium solution.

The system for forming and administering the RTU pantoprazole sodium solution may also include a flexible conduit coupled to the first pouch, wherein the flexible conduit is in fluid communication with the first pouch for administering the RTU pantoprazole sodium solution out of the first pouch. Preferably, administering the RTU pantoprazole sodium solution out of the first pouch includes administering the RTU pantoprazole sodium solution intravenously to a subject.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
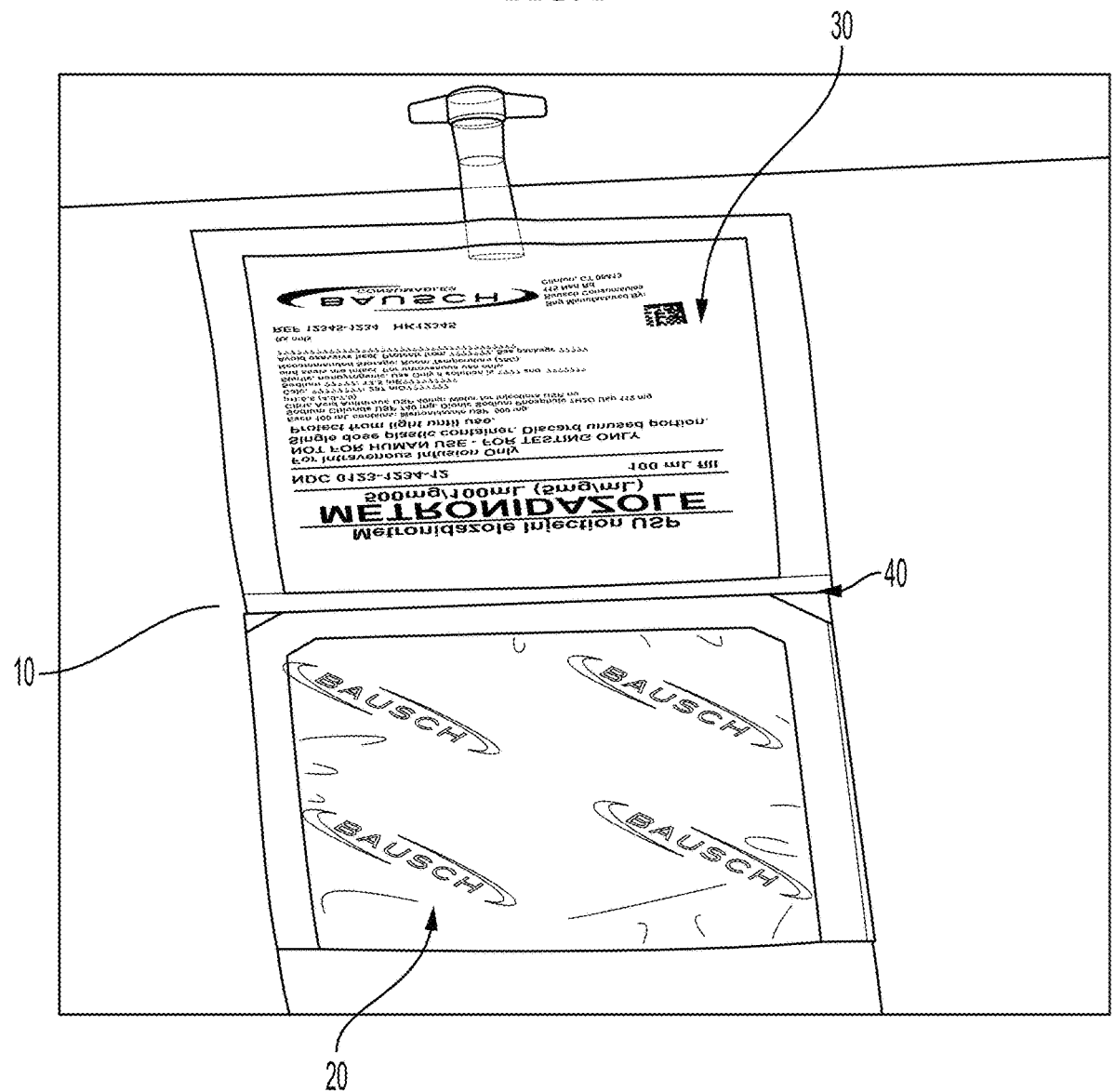
FIG. 1 is a photo of a flexible container 10 with two sealed compartments 20, 30 adjacent to each other having a frangible seal 40 therebetween, according to embodiments of the present invention.

The inventors have advantageously contemplated a composition of spray dried pantoprazole sodium for injection made of a few components that can be sterilely and stably stored as well as reconstituted in a pouch container which is easily connected for administration to a patient by injection.

Ideally, a medicinal formulation of pantoprazole is as simple (e.g., pure, having few additional ingredients) as possible. However, given the characteristics of the pantoprazole molecule, additives are necessary for manufacture as well as stability during storage. The pantoprazole has the chemical name 5-difluoromethoxy-2-[(3,4-dimethoxy-2-pyridinyl)methylsulfinyl]-1H-benzimidazole and is a chiral compound. As utilized herein, the term pantoprazole includes the pure enantiomers of pantoprazole and their mixtures in any mixing ratio. (S)-pantoprazole [(−)-pantoprazole] may be mentioned by way of example. Pantoprazole is present here as such or in the form of its salt with a base. Examples of salts with a base which may be mentioned are sodium, potassium, magnesium and calcium salts. Pantoprazole and/or a salt thereof may contain various amounts of solvent when isolated in crystalline form. In connection with the invention pantoprazole also refers to all solvates and in particular to hydrates of 5-difluoromethoxy-2-[(3,4-dimethoxy-2-pyridinyl)methylsulfinyl]-1H-benzimidazole and salts thereof. In certain embodiments, the pantoprazole includes pantoprazole sodium sesquihydrate.

Lyophilization is a commonly used process for preparing the hydrolytically labile pantoprazole sodium for storage prior to use. Typically, the lyophilized pantoprazole sodium is reconstituted in solution prior to use—e.g., injection into the patient. Because the dosage of the pantoprazole sodium is milligram quantities, lyophilization of a single dose alone is ineffective, requiring the addition of a bulking agent. Bulking agents that improve the lyophilization process also increase the manufacturing cost and can affect the stability and effectiveness of the pantoprazole active ingredient. While freeze drying of pantoprazole has been previously carried out using various bulking agents, the inventors have discovered that using a spray drying technique for pantoprazole in the presence of a bulking agent (e.g., sodium chloride (NaCl)) renders a highly stable pantoprazole sodium blend powder made from few components. In particular, the use of sodium chloride as the bulking agent for addition to and spray drying of the pantoprazole composition renders a more effective drying process than freeze drying or lyophilization.

In certain embodiments, the inventors contemplate a spray-dried storage stable pantoprazole composition include a pantoprazole and an excipient matrix comprising sodium chloride with the pantoprazole substantially uniformly dispersed in the excipient matrix. The phrase "substantially uniformly dispersed" with reference to the "excipient matrix" means that any first portion of the composition includes pantoprazole in a first amount relative to the weight of the first position, any second portion of the composition different than the first portion includes pantoprazole in a second amount relative to the weight of the second position, and the amounts of the first portion and the second portion are within 10%, 5%, 3%, 2%, or 1% of each other. It is to be appreciated that during the process of forming the pantoprazole composition, the sodium chloride may be included as part of the bulking agent. Upon formation of the pantoprazole composition, the same sodium chloride may be part of the excipient matrix by which the pantoprazole is substantially uniformly dispersed therein. It has been surprisingly found that substantial uniform dispersion of the pantoprazole in the excipient matrix including sodium chloride can be achieved by spray-drying. Further, it is contemplated that the forming the pantoprazole composition including sodium chloride by spray-drying results in a storage stable composition. Methods for forming the pantoprazole composition, along with kits including the pantoprazole composition, are also provided herein.

Without being bound by theory, inventors contemplate that spray-drying can effectively reduce the particle size of the pantoprazole. This reduced particle size can lead to improved blending with the bulking agent thereby leading to improved accuracy of dosing of the pantoprazole as compared to compositions formed using conventional drying methods (e.g. freeze drying or lyophilization). Specifically, as well known in the art, freeze drying and lyophilization rely on a low temperature dehydration process after freezing of the conventional pantoprazole composition to remove water at an interface of the conventional pantoprazole composition exposed to the environment. As this process progresses, the interface continues to move through the conventional pantoprazole composition thereby exposing its pantoprazole to the interface and environment. This exposure can lead to degradation of its pantoprazole. Beyond stability, spray-drying can improve dissolution kinetics of the pantoprazole as compared to conventional drying methods (e.g. freeze drying or lyophilization) due to the decrease in particle size of the pantoprazole.

Furthermore, the pantoprazole composition, after storage, exhibits minimal formation of degradants. It is contemplated herein that the minimization of the formation of degradants is at least due to spray-drying and the excipient matrix including sodium chloride. As described above, the bulking agent including sodium chloride improves uniformity of the dispersion of the pantoprazole in the excipient matrix. In addition, without being bound by theory, the excipient matrix including at least the same sodium chloride may improve storage stability of the pantoprazole as compared to compositions free of sodium chloride. In contrast to the inventive compositions described herein, conventional methods rely on refrigeration of aqueous compositions including pantoprazole that results in inadequate storage stability. As described in greater detail below, the spray-dried storage stable pantoprazole composition can be stored in dry form (e.g. powder form) at elevated temperatures while still maintaining improved accuracy of dosing of the pantoprazole.

In various embodiments, the composition, after storage at 25° C. and 40% relative humidity for 12 weeks, contains equal or less than 0.20%, equal or less than 0.15%, or equal or less than 0.10%, by weight of a pantoprazole sulfone degradant based on a total weight of the composition. In these and other embodiments, the composition, after storage at 25° C. and 40% relative humidity for 12 weeks, contains equal or less than 1%, equal or less than 0.75%, or equal or less than 0.50%, by weight of total impurities (e.g. degradants) based on a total weight of the composition. Non-limiting example of contemplated impurities of pantoprazole are shown in Table 1.

TABLE 1

Impurities of Pantoprazole

| Name of Impurity | Chemical name | Type of Impurity |
| --- | --- | --- |
| Related Compound-A (Pantoprazole sulfone) | 5-(difluoromethoxy)-2-[[(3,4-dimethoxy-2-pyridyl) methyl] sulphonyl)]-1H-benzimidazole | Degradant |
| Related compound-B (Pantoprazole sulfide) | 5-(difluoromethoxy)-2-[[(3,4-dimethoxy-2-pyridyl) methyl]thio]-1H-benzimidazole | Process |

TABLE 1-continued

Impurities of Pantoprazole

| Name of Impurity | Chemical name | Type of Impurity |
|---|---|---|
| Related Compound-C (Benzimidazolethiol derivative) | 5-(difluoromethoxy)-1H-benzimidazole-2-thiol | Process |
| Related Compound-D (N1-Methyl pantoprazole) | 5-(difluoromethoxy)-2-[(RS)-[(3,4-dimethoxypyridin-2-yl)methyl] Sulfinyl]-1-methyl-1H-benzimidazole | Degradant |
| Related Compound-F (N3-Methylpantoprazole) | 6-(difluoromethoxy)-2-[((RS)-[(3,4-dimethoxypyridin-2-yl)methyl] Sulfinyl]-1-methyl-1H-benzimidazole | Degradant |
| Related Compound-E (Pantoprazole dimer) | Mixture of the stereoisomers of 6,6'-bis (Difluoro methoxy)-2,2'-bis[[(3,4-dimethoxypyridin-2yl) methyl] sulfinyl]-1H,1'H-5,5'-bibenzimidazolyl | Process |

In addition to sodium chloride, the excipient matrix may include a salt different than sodium chloride, an amino acid, a sugar, or combinations thereof. The salt different than sodium chloride may include magnesium chloride ($MgCl_2$), calcium chloride ($CaCl_2$)), or a combination thereof. The amino acid may include glycine. The sugar may include dextrose, sucrose, trehalose, or combinations thereof. In certain embodiments, the excipient matrix consists essentially of, or consists of, NaCl. It is to be appreciated that other components, such as pH modifiers (e.g. sodium hydroxide (NaOH)), are not excipients of the excipient matrix. In various embodiments, the pantoprazole and the sodium chloride are present in the composition in a weight ratio of from about 1:100 to about 1:1, from about 1:50 to about 1:5, or from about 1:20 to about 1:10.

Figure 2:
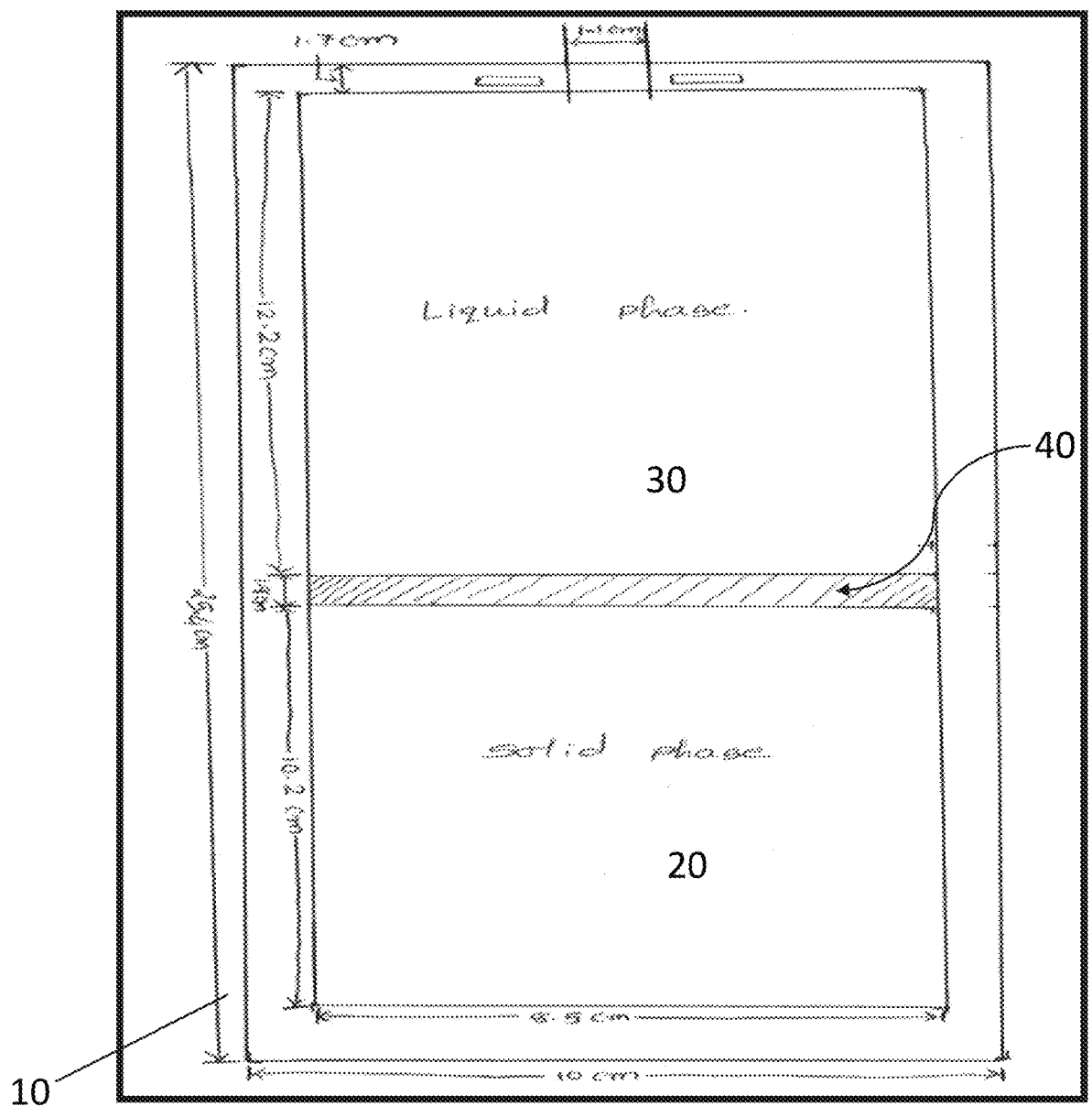
FIG. 2 is a schematic of a flexible container 10 with two sealed compartments 20, 30 adjacent to each other having a frangible seal 40 therebetween, according to embodiments of the present invention.

As introduced above and shown in FIGS. 1 and 2, the inventors have contemplated a kit including the storage stable pantoprazole composition and a liquid phase, along with a method of making the same. The kit (e.g. including a flexible container 10) may be a ready-to-use (RTU) pantoprazole sodium for injection including aseptically providing the stabilized pantoprazole sodium blend powder to a first chamber of a first pouch 20 and sealing the first pouch 20 with the pantoprazole composition therein, and aseptically providing sterile water as the liquid phase to a second chamber of a second pouch 30 and sealing the second pouch 30 with the sterile water therein. In various embodiments, the flexible container 10 includes the first pouch 20 and the second pouch 30 with the first and second chambers as two sealable chambers adjacent to each other having a frangible seal 40 therebetween. In certain embodiments, the sealing of the first and second chambers is carried in the presence of nitrogen gas. The flexible container may be made of or includes a polymeric material including aluminum.

View from another perspective, the storage stable pantoprazole composition may be contained in the first chamber of the first pouch 20 including the polymeric material. The storage stable pantoprazole composition may be present in the first chamber in an amount of from about 20 to about 100 mg, from about 30 mg to about 90 mg, or from about 40 mg to about 80 mg. The liquid phase may be contained in the second chamber of the second pouch 30 including the polymeric material. In certain embodiments, the liquid phase comprises water. The liquid phase may be present in the second chamber in an amount of from about 10 to about 200 mL. In various embodiments, the first pouch 20 and the second pouch 30 are coupled together and the first chamber and the second chamber are isolated from each other.

In additional embodiments, the flexible container 10 has a vertical orientation in which the first pouch 20 is aligned beneath the second pouch 30 with the frangible seal 40 forming both a topmost side of the first pouch 20 and a bottommost side of the second pouch 30. This orientation allows for the reconstituted solution of the storage stable pantoprazole composition in the lower (bottom) first pouch 20 with the water from the second pouch 30 to be administered from the lower first pouch 20 through a flexible conduit or tubing to an intravenous needle or port into the patient. For example, the flexible container 10 may be attached to a pole (e.g. an I.V. pole) and then the reconstituted pantoprazole composition can be administered from the first pouch 20 to the patient. In exemplary embodiments, 40 mg or 80 mg of the pantoprazole composition or a batch multiple thereof is present in a ready-to-use (RTU) reconstituted pantoprazole solution for injection. In other embodiments, the sodium hydroxide is present in an amount of about 2 to 5 mg for each 40 mg or 80 mg dose of the pantoprazole. In certain embodiments, the sodium hydroxide is present in an amount of about 3 to 4 mg for each 40 mg or 80 mg dose of the pantoprazole.

In additional embodiments, the flexible container 10 includes or is made of a polymeric material including aluminum to protect and maintain stability of the pantoprazole composition. The first pouch 20 of the flexible container 10 may be or may be made from an opaque material to block light from reaching the pantoprazole. Additionally, the second pouch 30 may include a transparent material such that the sterile water therein can be visually monitored for contaminants prior to reconstitution and use.

As would be readily understood by the skilled person, the forming of the RTU pantoprazole solution includes breaking the frangible seal 40 between the first pouch 20 and the second pouch 30, thereby allowing the sterile water to combine with the storage stable pantoprazole composition in the first pouch 20 to thereby form the RTU pantoprazole solution.

The system for forming and administering the RTU pantoprazole solution may also include a flexible conduit coupled to the first pouch 20, wherein the flexible conduit is in fluid communication with the first pouch 20 for administering the RTU pantoprazole solution out of the first pouch 20. In various embodiments, administering the RTU pantoprazole solution out of the first pouch 20 includes administering the RTU pantoprazole solution intravenously to a subject.

A method for forming the storage stable pantoprazole composition includes combining a bulking agent and water to form a first solution and combining the pantoprazole and the first solution to form a second solution. The first and second solutions may be formed at a temperature of from about 1° C. to about 40° C. In particular, in one embodiment from about 1° C. to about 10° C. and in another embodiment from about 15° C. to about 30° C. The first and second solutions may be formed in the presence of an inert gas, such as nitrogen. The first and second solutions may be formed under agitation, such as mixing, for a period of time sufficient to form the solution (e.g. at least 1 minute, at least 5 minute, at least 30 minutes, at least 60 minutes, at least 120 minutes, 240 minutes, or at least 24 hours). The bulking agent may include a salt, an amino acid, a sugar, or combinations thereof. The salt may include sodium chloride (NaCl), magnesium chloride ($MgCl_2$), calcium chloride ($CaCl_2$)), or combinations thereof. The amino acid may include glycine. The sugar may include dextrose, sucrose, trehalose, or combinations thereof. In various embodiments, the pantoprazole and the bulking agent (e.g. sodium chloride) are present in the second solution in a weight ratio of from about 1:100 to about 1:1, from about 1:50 to about 1:5, or from about 1:20 to about 1:10.

The method further includes combining a pH modifier (e.g. sodium hydroxide) and the second solution to form a bulk solution. The pH modifier is combined with the second solution in an amount sufficient for the bulk solution to have a pH of from about 8 to about 10. The bulk solution may be formed at a temperature of from about 1° C. to about 40° C. In particular, in one embodiment from about 1° C. to about 10° C. and in another embodiment from about 15° C. to about 30° C. The bulk solution may be formed in the presence of an inert gas, such as nitrogen. The bulk solution may be formed under agitation, such as mixing, for a period of time sufficient to form the solution (e.g. at least 1 minute, at least 5 minute, at least 30 minutes, at least 60 minutes, at least 120 minutes, 240 minutes, or at least 24 hours).

The method further includes removing water from the bulk solution by drying to form the storage stable pantoprazole composition. The step of removing the water from the bulk solution by drying includes spray-drying, spray solidification, spray pilling, or combinations thereof. In certain embodiments, spray-drying is utilized to dry the storage stable pantoprazole composition.

Spray-drying may be carried out using any method know in the art suitable for drying the storage stable pantoprazole composition. Suitable methods can be found in K. Masters, Spray Drying Handbook, 5th Ed. 1991, and J. Broadhead, S. K. Edmond Ronan, C. T. Rhodes, The Spray Drying of Pharmaceuticals, Drug Dev. Ind. Pharm. 18, 1169 (1992). The process of spray-drying includes dispersing a solution or suspension of the product to be dried into fine droplets and drying it with a hot stream of gas. The solid component remaining after evaporation of the solvent is removed from the stream of gas by a cyclone and/or by a filter unit and collected.

Spray drying may include a set of parameters that are implemented in the spray drying process by the spray dryer, wherein the set of parameters include an inlet temperature of 120 to 220° C., an outlet temperature of 60 to 90° C., a flow rate (e.g., Q-flow) of about 30 to 65 mm, and a feed rate of about 20 to 40%. Preferably, the set of parameters that are implemented in the spray drying process by the spray dryer include an inlet temperature of 145 to 180° C., an outlet temperature of 86 to 89° C., a flow rate of about 65 mm, and a feed rate of about 20 to 40%.

In other embodiments, the step of combining the pH modifier (e.g. sodium hydroxide) and the second solution is further defined as forming a third solution, and wherein the method further includes combining a solvent and the third solution to form the bulk solution. In these embodiments, the third and bulk solutions may be formed at a temperature of from about 1° C. to about 40° ° C. In particular, in one embodiment from about 1° C. to about 10° C. and in another embodiment from about 15° C. to about 30° C. The third and bulk solutions may be formed in the presence of an inert gas, such as nitrogen. The third and bulk solutions may be formed under agitation, such as mixing, for a period of time sufficient to form the solution (e.g. at least 1 minute, at least 5 minute, at least 30 minutes, at least 60 minutes, at least 120 minutes, 240 minutes, or at least 24 hours). In various embodiments, the solvent comprises acetone.

In various embodiments, the solvent may include an azeotropic agent, such as an acetonitrile solution. In one embodiment, about 40 to about 60 ml of acetonitrile solution is added to the third solution as disclosed herein. An azeotropic agent like acetonitrile is added to ensure that the entire pantoprazole blend is processed through the spray dryer homogenously as one mixture having one boiling point, as opposed to being processed based on the boiling point of each component in the blend. In additional embodiments, to ensure undissolved particles are removed, the third solution is filtered prior to the addition of the azeotropic agent.

In additional embodiments, the contemplated method includes providing and processing a solution of water and the azeotropic agent through the spray dryer prior to providing the pantoprazole sodium blend solution to the spray dryer. Flushing the spray dryer with the blank solution of the pantoprazole sodium blend further aides in spraying drying a homogenous and uniform powder product of pantoprazole sodium including sodium hydroxide and the bulking agent. Preferably, the azeotropic agent is acetonitrile.

Examples

Figure 3:
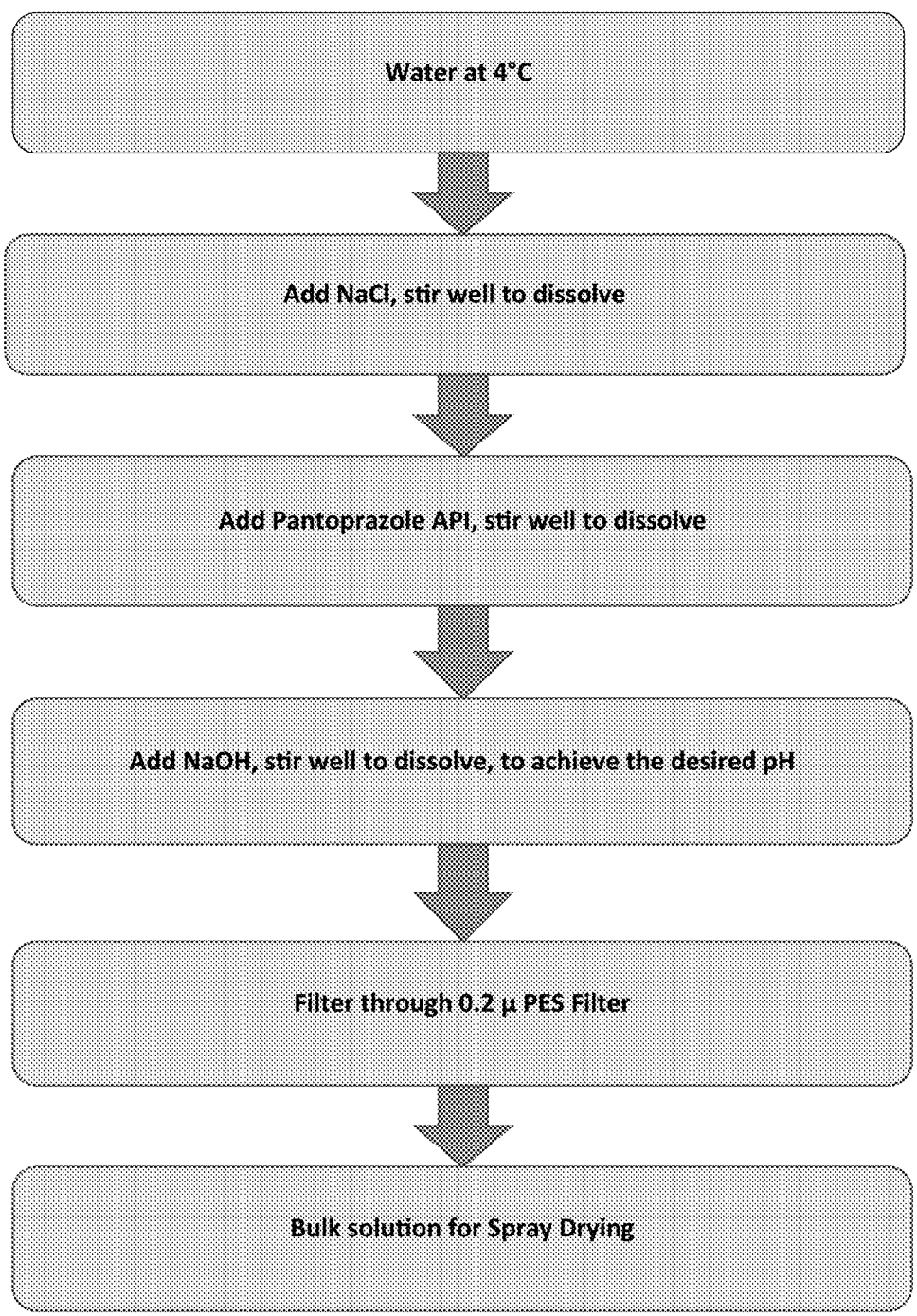
FIGS. 3 and 4 are flow charts of the contemplated method as disclosed herein according to embodiments of the present invention.
Figure 4:
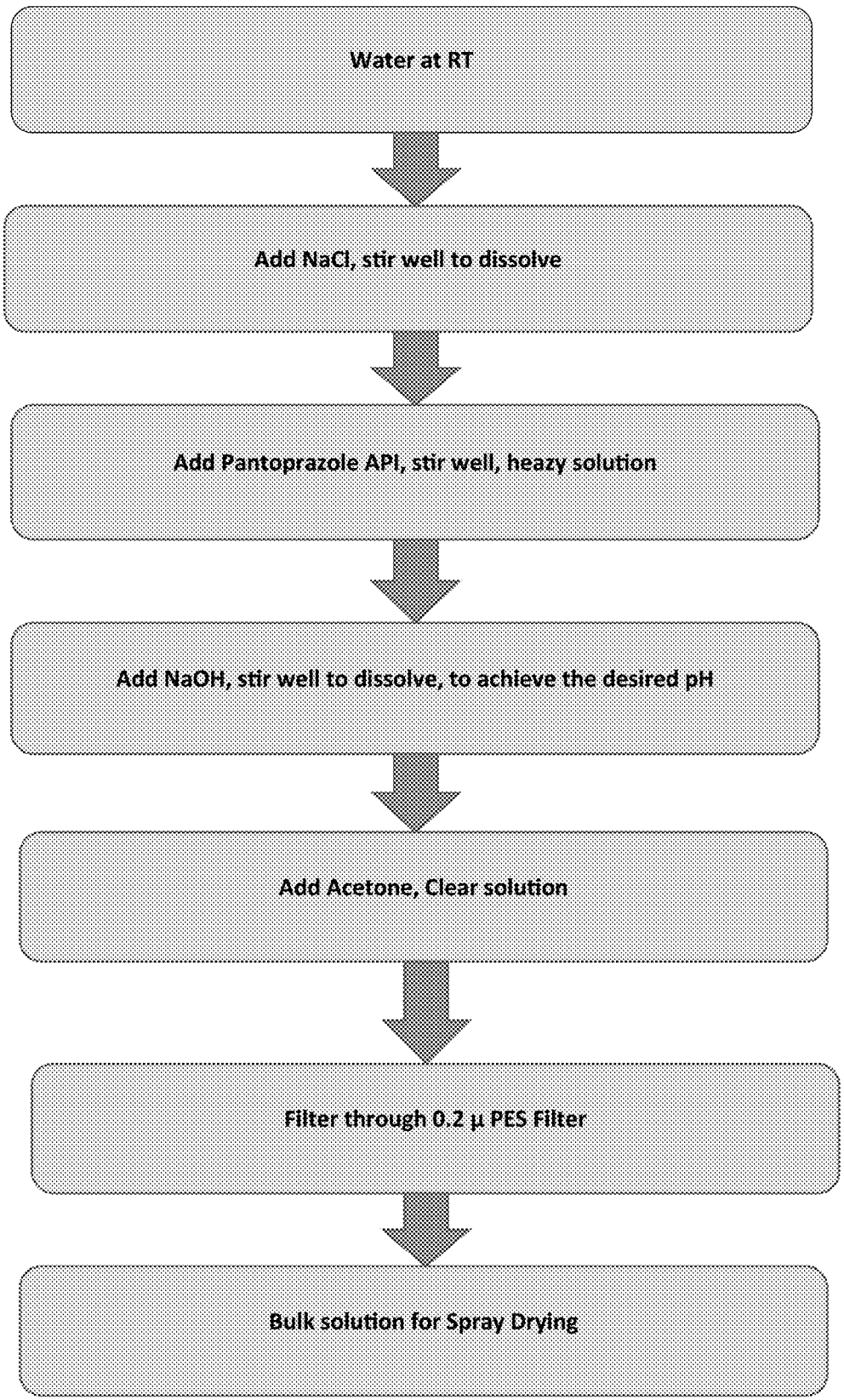

Exemplary spray-dried storage stable pantoprazole compositions were formed including the components as set forth in Formulations 1A, 1B, and 2 in Table 2A and 3A below using the parameters as set forth in Tables 2B and 3B based on Blending Processes I and II described below (see FIGS. 3 and 4). The bulk solutions prior to spray drying were formed under the following condition:

Ex. Comp. 1, 7, 13, and 19—Bulk solutions prepared at 25° C. and then spray dried.

Ex. Comp. 2, 8, 14, and 20—Bulk solutions prepared at 25° C. and then spray dried.

Ex. Comp. 3, 9, 15, and 21—Bulk solutions prepared at 4° C. and then spray dried.

Ex. Comp. 4, 10, 16, and 22—Bulk solutions prepared at 4° C. and then spray dried. The powdered pantoprazole compositions after spray drying were then exposed to 30° C./65% Rh for 7.30 hours.

Ex. Comp. 5, 11, 17, and 23—Bulk solutions prepared at 4° C. with 50% less NaCl and then spray dried.

Ex. Comp. 6, 12, 18, and 24—Bulk solution prepared in water and acetone and spray dried.

For Blending Process I, a bulk solution was formed according to Table 3A. Water at a temperature of 4° C. was combined with sodium chloride and stirred until the sodium chloride was dissolved to form a first solution. Pantoprazole sodium sesquihydrate was combined with the first solution and stirred until the pantoprazole sodium sesquihydrate was dissolved to form a second solution. Sodium hydroxide was combined with the second solution and stirred until the sodium hydroxide was dissolved to form a bulk solution having the desired pH. The bulk solution was then filtered through a 0.2 µPES filter. The filtered bulk solution was then spray-dried according to Table 2B to form the exemplary spray-dried storage stable pantoprazole compositions.

For Blending Process II, a bulk solution was formed according to Table 3B. Water at a temperature of 4° C. was combined with sodium chloride and stirred until the sodium chloride was dissolved to form a first solution. Pantoprazole sodium sesquihydrate was combined with the first solution and stirred until the pantoprazole sodium sesquihydrate was at least partially dissolved to form a second solution (heavy solution). Sodium hydroxide was combined with the second solution and stirred until the sodium hydroxide was dissolved to form a third solution having the desired pH. Acetone was combined with the third solution to form a bulk solution. The bulk solution was then filtered through a 0.2 µPES filter. The filtered bulk solution was then spray-dried according to 3B to form the exemplary spray-dried storage stable pantoprazole compositions.

After spray-dry, each of the exemplary spray-dried storage stable pantoprazole compositions was filled in a duplex IV bag. One chamber of each bag filled with spray dry powder containing 40 mg of the pantoprazole composition and sealed with a hand sealer. Another chamber was filled with water and closed with a twist off port. There were two bags for each stability station. The bags were stored at various conditions for stability testing At each evaluation time point, one bag was directly admixed with the water and the resulting solution was evaluated ("Analysis of Pantoprazole Composition without Liquid Phase") while another bag was evaluated as a powder without the water ("Analysis of Pantoprazole Composition combined with Liquid Phase"). The results of the evaluations for storage stability for a period of 3 months under various processing and storage conditions are shown in Tables 4A-C, 5A-C, 6A-C, and 7A-C.

In view of the evaluations, the exemplary spray-dried storage stable pantoprazole compositions contain equal or less than 0.20% by weight of a pantoprazole sulfone degradant based on a total weight of the compositions and contain equal or less than 1% by weight of total impurities based on a total weight of the compositions after 2 months of stability testing. Further a majority of the exemplary spray-dried storage stable pantoprazole compositions exhibit excellent storage stability after 3 months of stability testing.

TABLE 2A

Bulk Solution Formulation IA and IB

| Component | Exemplary Ingredient | Formulation 1A Amount | Formulation 1B Amount |
|---|---|---|---|
| Vehicle | Water | 800 mL | 800 mL |
| Bulking Agent | NaCl | 36.0 grams | 18.0 grams |
| Pantoprazole | Pantoprazole Sodium Sesquihydrate | 1.8 grams | 1.8 grams |
| pH Modifier | NaOH | 34.0 grams | 34.0 grams |

Pantoprazole sodium sesquihydrate was from MSN Laboratories Pvt. Ltd., API molecular formula: $C_{16}H_{14}F_2N_3NaO_4S$, 1.5 $H_2O$, chemical name: 1H-Benzimidazole, 5-(difluoromethoxy)-2-[[(3,4-dimethoxy-2-pyridinyl) methyl] sulfinyl]-sodium salt, sesquihydrate.
Sodium chloride (NaCl) is commercially available from Avantor-J. T. Baker.
Sodium hydroxide (NaOH) is commercially available from Sigma Aldrich.

TABLE 2B

Spray-Drying Parameters I

| Parameters | Conditions |
|---|---|
| Instruments | Buchi Instrument B-290 + Dehumidifier B-296, Open Mode |
| Cyclone | Standard |
| Aspirator | 100% |
| Q-Flow | 40 mm |
| Pump | 10% |
| Inlet Temp | 155-170° C. |
| Outlet Temp | 104-108° C. |
| Spray Gas | Nitrogen |
| Outlet Filter | Polyester |
| Feed Tubing | Silicone |
| Nozzle | Two Fluid |

TABLE 3A

Bulk Solution Formulation II

| Component | Exemplary Ingredient | Formulation II Amount |
|---|---|---|
| Vehicle | Water | 350 milliliters |
| Bulking Agent | NaCl | 36.0 grams |
| Pantoprazole | Pantoprazole Sodium Sesquihydrate | 1.8 grams |
| pH Modifier | NaOH | 34.0 grams |
| Solvent | Acetone | 500 milliliters |

Pantoprazole sodium sesquihydrate was from MSN Laboratories Pvt. Ltd., API molecular formula: $C_{16}H_{14}F_2N_3NaO_4S$, 1.5 $H_2O$, chemical name: 1H-Benzimidazole, 5-(difluoromethoxy)-2-[[(3,4-dimethoxy-2-pyridinyl) methyl] sulfinyl]-sodium salt, sesquihydrate.
Sodium chloride (NaCl) is commercially available from Avantor-J. T. Baker.
Sodium hydroxide (NaOH) is commercially available from Sigma Aldrich.
Acetone is commercially available.

TABLE 3B

Spray-Drying Parameters II

| Parameters | Conditions |
|---|---|
| Instruments | Buchi Instrument B-290 + Dehumidifier B-296 + Inert Loop B-295, Closed Mode |
| Cyclone | Standard |
| Aspirator | 100% |
| Q-Flow | 40 mm |
| Pump | 10% |
| Inlet Temp | 85-95° C. |
| Outlet Temp | 65-70° C. |
| Spray Gas | Nitrogen |
| Outlet Filter | Polyester |
| Feed Tubing | Tygon MH 2375 |
| Nozzle | Two Fluid |

TABLE 4A

Stability Testing at 2-8° C. of Pantoprazole Compositions formed from Bulk Solutions Processed under Various Conditions

| Bulk Solution Formulation | | Exemplary Composition 1<br>IA | | | Exemplary Composition 2<br>IA | | |
|---|---|---|---|---|---|---|---|
| Blending Process | | Process I | | | Process I | | |
| Bulk Solution Temperature | | 25° C. | | | 25° C. | | |
| Condition | | Initial | 1 Month<br>2-8° C. | 3 Months<br>2-8° C. | Initial | 1 Month<br>2-8° C. | 3 Months<br>2-8° C. |
| Analysis of Pantoprazole Composition without Liquid Phase | | | | | | | |
| Description | | White colored powder | White colored powder | White colored powder | White colored powder | White colored powder | White colored powder |
| Water content | | 0.500 | 0.555 | 0.545 | 0.555 | 0.705 | 0.590 |
| Assay - Pantoprazole | | 99.2 | 95.7 | 95.1 | 99.2 | 99.4 | 93.0 |
| RS | Imp A | 0.07 | 0.06 | 0.07 | 0.07 | 0.07 | 0.07 |
| | Imp B | ND | ND | ND | ND | ND | ND |
| | Imp D&F | 0.06 | 0.06 | 0.10 | 0.06 | 0.14 | 0.12 |
| | Imp E | 0.01 | 0.02 | 0.01 | 0.01 | ND | 0.01 |
| | SMI | 0.03 | 0.02 | 0.02 | 0.03 | 0.04 | 0.02 |
| | Imp C | 0.01 | 0.00 | 0.02 | 0.01 | ND | 0.02 |
| | Total (Excluding Imp C) | 0.24 | 0.26 | 0.26 | 0.24 | 0.25 | 0.27 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.58 | 9.44 | 9.51 | 9.58 | 9.47 | 9.49 |
| Osmolality | | 279 | 280 | 296 | 273 | 276 | 293 |
| Assay - Pantoprazole | | NA | 100.9 | 99.9 | NA | NA | 98.6 |
| Assay - NaCl | | 99.8 | 98.5 | 100.8 | 99.3 | 102.2 | 100.4 |
| RS | Imp A | NA | 0.08 | 0.08 | NA | 0.07 | 0.07 |
| | Imp B | NA | ND | ND | NA | ND | ND |
| | Imp D&F | NA | 0.10 | 0.14 | NA | 0.11 | 0.15 |
| | Imp E | NA | 0.01 | 0.01 | NA | 0.01 | 0.01 |
| | SMI | NA | 0.07 | 0.08 | NA | 0.07 | 0.05 |
| | Imp C | NA | 0.02 | 0.03 | NA | 0.03 | 0.02 |
| | Total (Excluding Imp C) | NA | 0.36 | 0.44 | NA | 0.35 | 0.39 |
| LPC TEST 1A | 10 μm | NA | Complies | Complies | NA | Complies | Complies |
| | 25 μm | NA | | | NA | | |

TABLE 4B

Stability Testing at 2-8° C. of Pantoprazole Compositions formed from Bulk Solutions Processed under Various Conditions (cont.)

| Bulk Solution Formulation | | Exemplary Composition 3<br>IA | | | Exemplary Composition 4<br>IA | | |
|---|---|---|---|---|---|---|---|
| Blending Process | | Process I | | | Process I | | |
| Bulk Solution Temperature | | 4° C. | | | 4° C., Exposed to 30/65 for 7.30 hr | | |
| Condition | | Initial | 1 Month<br>2-8° C. | 3 Months<br>2-8° C. | Initial | 1 Month<br>2-8° C. | 3 Months<br>2-8° C. |
| Analysis of Pantoprazole Composition without Liquid Phase | | | | | | | |
| Description | | White colored powder | White colored powder | White colored powder | White colored powder | White colored powder | White colored powder |
| Water content | | 0.489 | 0.797 | 0.595 | 0.571 | 0.581 | 0.494 |
| Assay - Pantoprazole | | 98.9 | 97.2 | 92.1 | 96.5 | 90.6 | 92.3 |
| RS | Imp A | 0.07 | 0.06 | 0.07 | 0.05 | 0.02 | 0.06 |
| | Imp B | ND | ND | ND | ND | ND | 0.01 |
| | Imp D&F | 0.05 | 0.06 | 0.11 | 0.06 | 0.10 | 0.14 |
| | Imp E | 0.01 | 0.02 | 0.01 | 0.01 | 0.01 | 0.01 |

TABLE 4B-continued

Stability Testing at 2-8° C. of Pantoprazole Compositions formed
from Bulk Solutions Processed under Various Conditions (cont.)

| Bulk Solution Formulation | | Exemplary Composition 3 IA | | | Exemplary Composition 4 IA | | |
|---|---|---|---|---|---|---|---|
| Blending Process | | Process I | | | Process I | | |
| Bulk Solution Temperature | | 4° C. | | | 4° C., Exposed to 30/65 for 7.30 hr | | |
| Condition | | Initial | 1 Month 2-8° C. | 3 Months 2-8° C. | Initial | 1 Month 2-8° C. | 3 Months 2-8° C. |
| | SMI | | 0.03 | 0.02 | 0.02 | 0.02 | 0.03 | 0.03 |
| | Imp C | | 0.01 | 0.00 | 0.01 | 0.01 | 0.02 | 0.03 |
| | Total (Excluding Imp C) | | 0.22 | 0.26 | 0.27 | 0.23 | 0.32 | 0.32 |
| Analysis of Pantoprazole Composition combined with Liquid Phase | | | | | | | |
| Description | | | Clear Colorless Solution | Clear Colorless Solution | Clear Colorless Solution | Clear Colorless Solution | Clear Colorless Solution | Clear Colorless Solution |
| pH | | | 9.67 | 9.46 | 9.56 | 9.09 | 8.75 | 8.95 |
| Osmolality | | | 273 | 291 | 294 | 281 | 289 | 300 |
| Assay - Pantoprazole | | | NA | 102.3 | 99.1 | NA | 95.6 | 100.4 |
| Assay - NaCl | | | 99.0 | 100.4 | 100.2 | 99.7 | 100 | 99.2 |
| RS | Imp A | | NA | ND | 0.08 | NA | NA | 0.02 |
| | Imp B | | NA | ND | ND | NA | NA | ND |
| | Imp D&F | | NA | ND | 0.15 | NA | NA | 0.05 |
| | Imp E | | NA | ND | 0.01 | NA | NA | 0.00 |
| | SMI | | NA | ND | 0.05 | NA | NA | 0.01 |
| | Imp C | | NA | ND | 0.02 | NA | NA | 0.01 |
| | Total (Excluding Imp C) | | NA | ND | 0.36 | NA | NA | 0.02 |
| LPC TEST 1A | 10 μm | | NA | Complies | Complies | NA | Complies | Complies |
| | 25 μm | | NA | | | NA | | |

TABLE 4C

Stability Testing at 2-8° C. of Pantoprazole Compositions formed from Bulk
Solutions Processed under Various Conditions (cont.)

| Bulk Solution Formulation | | Exemplary Composition 5 IB | | | Exemplary Composition 6 II | | |
|---|---|---|---|---|---|---|---|
| Blending Process | | Process I | | | Process II | | |
| Bulk Solution Temperature | | 4° C., with 0.45% NaCl | | | Water and Acetone | | |
| Condition | | Initial | 1 Month 2-8° C. | 3 Months 2-8° C. | Initial | 1 Month 2-8° C. | 3 Months 2-8° C. |
| Analysis of Pantoprazole Composition without Liquid Phase | | | | | | | |
| Description | | White colored powder | White colored powder | White colored powder | White colored powder | White colored powder | White colored powder |
| Water content | | 0.687 | 0.842 | 0.952 | NA | 0.814 | NA |
| Assay - Pantoprazole | | 97.2 | 90.2 | 87.4 | 100.4 | 99.2 | NA |
| RS | Imp A | 0.05 | 0.05 | 0.01 | 0.05 | 0.05 | NA |
| | Imp B | ND | ND | 0.01 | ND | ND | NA |
| | Imp D&F | 0.06 | 0.20 | 0.13 | 0.02 | 0.03 | NA |
| | Imp E | 0.01 | 0.03 | ND | 0.01 | 0.02 | NA |
| | SMI | 0.02 | 0.06 | 0.03 | 0.02 | 0.01 | NA |
| | Imp C | 0.01 | 0.01 | 0.02 | ND | 0.01 | NA |
| | Total (Excluding Imp C) | 0.19 | 0.47 | 0.20 | 0.16 | 0.14 | NA |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.62 | 9.21 | 9.31 | 9.36 | 9.16 | 9.17 |
| Osmolality | | 143 | 144 | 306 | 294 | 277 | 295 |
| Assay - Pantoprazole | | NA | 94.5 | 97.44 | 95.445 | 94.92 | 106.1 |
| Assay - NaCl | | 101.7 | 100 | 102.6 | NA | 97.2 | 100.4 |

TABLE 4C-continued

Stability Testing at 2-8° C. of Pantoprazole Compositions formed from Bulk Solutions Processed under Various Conditions (cont.)

| Bulk Solution Formulation<br>Blending Process<br>Bulk Solution Temperature | | Exemplary Composition 5<br>IB<br>Process I<br>4° C., with 0.45% NaCl | | | Exemplary Composition 6<br>II<br>Process II<br>Water and Acetone | | |
|---|---|---|---|---|---|---|---|
| Condition | | Initial | 1 Month<br>2-8° C. | 3 Months<br>2-8° C. | Initial | 1 Month<br>2-8° C. | 3 Months<br>2-8° C. |
| RS | Imp A | NA | NA | NA | 0.06 | 0.06 | 0.05 | 0.05 |
| | Imp B | NA | NA | NA | 0.00 | ND | ND | ND |
| | Imp D&F | NA | NA | NA | 0.13 | 0.03 | 0.04 | 0.03 |
| | Imp E | NA | NA | NA | 0.01 | 0.01 | 0.01 | 0.01 |
| | SMI | NA | NA | NA | 0.04 | 0.02 | 0.03 | 0.01 |
| | Imp C | NA | NA | NA | 0.02 | ND | 0.02 | 0.03 |
| | Total (Excluding Imp C) | NA | NA | NA | 0.31 | 0.21 | 0.18 | 0.11 |
| LPC TEST 1A | 10 μm | NA | NA | Complies | Complies | Complies | Complies | NA |
| | 25 μm | NA | | | | | | NA |

Note: Imp A row has values 0.06, 0.06, 0.05, 0.05 under Composition 6 columns (Initial, 1 Month, 3 Months - with one extra).

TABLE 5A

Stability Testing at 25° C. and Relative Humidity of 40% of Pantoprazole Compositions formed from Bulk Solutions Processed under Various Conditions

| Bulk Solution Formulation<br>Blending Process<br>Bulk Solution Temperature | | Exemplary Composition 7<br>IA<br>Process I<br>25° C. | | | Exemplary Composition 8<br>IA<br>Process I<br>25° C. | | |
|---|---|---|---|---|---|---|---|
| Condition | | Initial | 1 Month<br>25° C.<br>40% Rh | 3 Months<br>25° C.<br>40% Rh | Initial | 1 Month<br>25° C.<br>40% Rh | 3 Months<br>25° C.<br>40% Rh |
| Analysis of Pantoprazole Composition without Liquid Phase | | | | | | | |
| Description | | White colored powder | White colored powder | White colored powder | White colored powder | White colored powder | White colored powder |
| Water content | | 0.500 | 0.639 | 0.496 | 0.555 | 0.532 | 0.572 |
| Assay - Pantoprazole | | 99.2 | 98.6 | 94.5 | 99.2 | 97.4 | 97.44 |
| RS | Imp A | 0.07 | 0.08 | 0.07 | 0.07 | 0.08 | 0.07 |
| | Imp B | ND | ND | 0.02 | ND | ND | 0.01 |
| | Imp D&F | 0.06 | 0.09 | 0.12 | 0.06 | 0.09 | 0.17 |
| | Imp E | 0.01 | 0.01 | 0.01 | 0.01 | 0.01 | 0.01 |
| | SMI | 0.03 | 0.03 | 0.05 | 0.03 | 0.03 | 0.06 |
| | Imp C | 0.01 | 0.00 | 0.02 | 0.01 | 0.00 | 0.02 |
| | Total (Excluding Imp C) | 0.24 | 0.32 | 0.35 | 0.24 | 0.35 | 0.39 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.58 | 9.53 | 9.42 | 9.58 | 9.55 | 9.4 |
| Osmolality | | 279 | 289 | 290 | 273 | 282 | 288 |
| Assay - Pantoprazole | | Na | 93.4 | 93.8 | NA | 93.3 | 94.0 |
| Assay - NaCl | | 99.8 | 96.5 | 100.5 | 99.3 | 96.7 | 100.2 |
| RS | Imp A | NA | 0.08 | 0.04 | NA | 0.07 | 0.04 |
| | Imp B | NA | ND | 0.00 | NA | ND | 0.00 |
| | Imp D&F | NA | 0.13 | 0.11 | NA | 0.13 | 0.11 |
| | Imp E | NA | 0.01 | 0.10 | NA | 0.01 | 0.00 |
| | SMI | NA | 0.06 | 0.03 | NA | 0.08 | 0.03 |
| | Imp C | NA | 0.02 | 0.03 | NA | 0.03 | 0.02 |
| | Total (Excluding Imp C) | NA | 0.41 | 0.22 | NA | 0.50 | 0.22 |
| LPC TEST 1A | 10 μm | NA | Complies | Complies | NA | Complies | Complies |
| | 25 μm | NA | | | NA | | |

TABLE 5B

Stability Testing at 25° C. and Relative Humidity of 40% of Pantoprazole Compositions formed from Bulk Solutions Processed under Various Conditions (cont.)

| | | Exemplary Composition 9 | | | Exemplary Composition 10 | | |
|---|---|---|---|---|---|---|---|
| Bulk Solution Formulation | | IA | | | IA | | |
| Blending Process | | Process I | | | Process I | | |
| Bulk Solution Temperature | | 4° C. | | | 4° C. Exposed to 30/65 for 7.30 hr | | |
| Condition | | Initial | 1 Month 25° C. 40% Rh | 3 Months 25° C. 40% Rh | Initial | 1 Month 25° C. 40% Rh | 3 Months 25° C. 40% Rh |
| *Analysis of Pantoprazole Composition without Liquid Phase* | | | | | | | |
| Description | | White colored powder | White colored powder | White colored powder | White colored powder | White colored powder | brown powder |
| Water content | | 0.489 | 0.516 | 0.548 | 0.571 | 0.519 | 0.309 |
| Assay - Pantoprazole | | 98.9 | 97.0 | 96.1 | 96.5 | 95.13 | 91.56 |
| RS | Imp A | 0.07 | 0.08 | NA | 0.05 | 0.02 | 0.09 |
| | Imp B | ND | ND | 0.07 | ND | ND | 0.06 |
| | Imp D&F | 0.05 | 0.06 | ND | 0.06 | 0.09 | 0.53 |
| | Imp E | 0.01 | 0.09 | 0.17 | 0.01 | 0.01 | ND |
| | SMI | 0.03 | 0.01 | 0.01 | 0.02 | 0.03 | 0.08 |
| | Imp C | 0.01 | 0.00 | 0.03 | 0.01 | 0.02 | 0.34 |
| | Total (Excluding Imp C) | 0.22 | 0.32 | 0.02 | 0.23 | 0.02 | 1.39 |
| *Analysis of Pantoprazole Composition combined with Liquid Phase* | | | | | | | |
| Description | | Clear Colorless Solution | Clear Colorless Solution | Clear Colorless Solution | Clear Colorless Solution | Clear Colorless Solution | Clear Colorless Solution |
| pH | | 9.67 | 9.56 | 8.9 | 9.09 | 8.76 | 9.47 |
| Osmolality | | 273 | 291 | 289 | 281 | 294 | 287 |
| Assay - Pantoprazole | | NA | 90.9 | 92.4 | NA | 91.5 | 90.8 |
| Assay - NaCl | | 99.0 | 94.3 | 99.8 | 99.7 | 98.1 | 101.8 |
| RS | Imp A | NA | 0.07 | 0.08 | NA | NA | 0.06 |
| | Imp B | NA | ND | 0.01 | NA | NA | 0.01 |
| | Imp D&F | NA | 0.12 | 0.21 | NA | NA | 0.19 |
| | Imp E | NA | 0.02 | 0.01 | NA | NA | 0.01 |
| | SMI | NA | 0.06 | 0.05 | NA | NA | 0.06 |
| | Imp C | NA | 0.03 | 0.02 | NA | NA | 0.13 |
| | Total (Excluding Imp C) | NA | 0.40 | 0.45 | NA | NA | 0.51 |
| LPC TEST 1A | 10 μm | NA | Complies | Complies | NA | Complies | Complies |
| | 25 μm | NA | | | NA | | |

TABLE 5C

Stability Testing at 25° C. and Relative Humidity of 40% of Pantoprazole Compositions formed from Bulk Solutions Processed under Various Conditions (cont.)

| | | Exemplary Composition 11 | | | Exemplary Composition 12 | | |
|---|---|---|---|---|---|---|---|
| Bulk Solution Formulation | | IB | | | II | | |
| Blending Process | | Process I | | | Process II | | |
| Bulk Solution Temperature | | 4° C., with 0.45% NaCl | | | Water and Acetone | | |
| Condition | | Initial | 1 Month 25° C. 40% Rh | 3 Months 25° C. 40% Rh | Initial | 1 Month 25° C. 40% Rh | 3 Months 25°° C. 40% Rh |
| *Analysis of Pantoprazole Composition without Liquid Phase* | | | | | | | |
| Description | | White colored powder | White colored powder | White colored powder | White colored powder | White colored powder | NA |
| Water content | | 0.687 | 1.255 | 0.804 | NA | 0.717 | NA |
| Assay - Pantoprazole | | 97.2 | 95.34 | 89.145 | 100.4 | 99.7 | NA |
| RS | Imp A | 0.05 | 0.05 | 0.06 | 0.05 | 0.05 | NA |
| | Imp B | ND | ND | ND | ND | ND | NA |
| | Imp D&F | 0.06 | 0.16 | 0.18 | 0.02 | 0.05 | NA |
| | Imp E | 0.01 | 0.02 | 0.01 | 0.01 | 0.02 | NA |

TABLE 5C-continued

Stability Testing at 25° C. and Relative Humidity of 40% of Pantoprazole
Compositions formed from Bulk Solutions Processed under Various Conditions (cont.)

| Bulk Solution Formulation<br>Blending Process<br>Bulk Solution Temperature | | Exemplary Composition 11<br>IB<br>Process I<br>4° C., with 0.45% NaCl | | | Exemplary Composition 12<br>II<br>Process II<br>Water and Acetone | | |
|---|---|---|---|---|---|---|---|
| Condition | | Initial | 1 Month<br>25° C.<br>40% Rh | 3 Months<br>25° C.<br>40% Rh | Initial | 1 Month<br>25° C.<br>40% Rh | 3 Months<br>25°° C.<br>40% Rh |
| | SMI | 0.02 | 0.06 | 0.02 | 0.02 | 0.03 | NA |
| | Imp C | 0.01 | 0.02 | 0.02 | ND | 0.02 | NA |
| | Total (Excluding Imp C) | 0.19 | 0.44 | 0.32 | 0.16 | 0.17 | NA |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.62 | 9.11 | 9.18 | 9.36 | 9.24 | 9.21 |
| Osmolality | | 143 | 144 | 287 | 294 | 282 | 287 |
| Assay - Pantoprazole | | NA | 90.9 | 92.0 | 90.9 | 89.6 | 99.2 |
| Assay - NaCl | | 101.7 | 103.6 | 101.2 | NA | 98.5 | 100 |
| RS | Imp A | NA | NA | 0.06 | 0.06 | 0.05 | 0.05 |
| | Imp B | NA | NA | 0.00 | ND | ND | ND |
| | Imp D&F | NA | NA | 0.17 | 0.03 | 0.07 | 0.10 |
| | Imp E | NA | NA | 0.01 | 0.01 | 0.02 | ND |
| | SMI | NA | NA | 0.05 | 0.02 | 0.03 | 0.02 |
| | Imp C | NA | NA | 0.03 | ND | 0.02 | 0.06 |
| | Total (Excluding Imp C) | NA | NA | 0.36 | 0.21 | 0.19 | 0.19 |
| LPC TEST 1A | 10 μm | NA | Complies | Complies | Complies | Complies | NA |
| | 25 μm | NA | | | | | NA |

TABLE 6A

Stability Testing at 30° C. and Relative Humidity of 65% of Pantoprazole
Compositions formed from Bulk Solutions Processed under Various Conditions

| Bulk Solution Formulation<br>Blending Process<br>Bulk Solution Temperature | | Exemplary Composition 13<br>IA<br>Process I<br>25° C. | | | Exemplary Composition 14<br>IA<br>Process I<br>25° C. | | |
|---|---|---|---|---|---|---|---|
| Condition | | Initial | 1 Month<br>30° C.<br>65% Rh | 3 Months<br>30° C.<br>65% Rh | Initial | 1 Month<br>30° C.<br>65% Rh | 3 Months<br>30° C.<br>65% Rh |
| Analysis of Pantoprazole Composition without Liquid Phase | | | | | | | |
| Description | | White colored powder | White colored powder | White colored powder | White colored powder | White colored powder | White colored powder |
| Water content | | 0.500 | 0.598 | 0.464 | 0.555 | 0.614 | 0.560 |
| Assay - Pantoprazole | | 99.2 | 97.3 | 93.7 | 99.2 | 95.4 | 96.4 |
| RS | Imp A | 0.07 | 0.09 | 0.08 | 0.07 | 0.09 | 0.78 |
| | Imp B | ND | ND | ND | ND | ND | ND |
| | Imp D&F | 0.06 | 0.09 | 0.20 | 0.06 | 0.09 | 0.21 |
| | Imp E | 0.01 | 0.01 | 0.01 | 0.01 | 0.01 | 0.01 |
| | SMI | 0.03 | 0.03 | 0.04 | 0.03 | 0.05 | 0.04 |
| | Imp C | 0.01 | 0.00 | ND | 0.01 | 0.00 | ND |
| | Total (Excluding Imp C) | 0.24 | 0.34 | 0.39 | 0.24 | 0.36 | 1.09 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.58 | 9.56 | 9.23 | 9.58 | 9.5 | 9.16 |
| Osmolality | | 279 | 292 | 278 | 273 | 285 | 274 |
| Assay - Pantoprazole | | Na | 96.0 | 95.9 | NA | 96.5 | 97.3 |
| Assay - NaCl | | 99.8 | 97.9 | 99.2 | 99.3 | 98.3 | 98.4 |

TABLE 6A-continued

Stability Testing at 30° C. and Relative Humidity of 65% of Pantoprazole
Compositions formed from Bulk Solutions Processed under Various Conditions

| Bulk Solution Formulation<br>Blending Process<br>Bulk Solution Temperature | | Exemplary Composition 13<br>IA<br>Process I<br>25° C. | | | Exemplary Composition 14<br>IA<br>Process I<br>25° C. | | |
|---|---|---|---|---|---|---|---|
| Condition | | Initial | 1 Month<br>30° C.<br>65% Rh | 3 Months<br>30° C.<br>65% Rh | Initial | 1 Month<br>30° C.<br>65% Rh | 3 Months<br>30° C.<br>65% Rh |
| RS | Imp A | NA | 0.08 | 0.08 | NA | 0.08 | 0.08 |
| | Imp B | NA | ND | ND | NA | ND | ND |
| | Imp D&F | NA | 0.14 | 0.25 | NA | 0.14 | 0.25 |
| | Imp E | NA | 0.01 | ND | NA | 0.01 | ND |
| | SMI | NA | 0.08 | 0.06 | NA | 0.08 | 0.15 |
| | Imp C | NA | 0.03 | 0.05 | NA | 0.03 | 0.05 |
| | Total (Excluding Imp C) | NA | 0.50 | 0.46 | NA | 0.43 | 0.61 |
| LPC TEST 1A | 10 μm | NA | Complies | Complies | NA | Complies | Complies |
| | 25 μm | NA | | | NA | | |

TABLE 6B

Stability Testing at 30° C. and Relative Humidity of 65% of Pantoprazole
Compositions formed from Bulk Solutions Processed under Various Conditions (cont.)

| Bulk Solution Formulation<br>Blending Process<br>Bulk Solution Temperature | | Exemplary Composition 15<br>IA<br>Process I<br>4° C. | | | Exemplary Composition 16<br>IA<br>Process I<br>4° C., Exposed to 30/65 for 7.30 hr | | |
|---|---|---|---|---|---|---|---|
| Condition | | Initial | 1 Month<br>30° C.<br>65% Rh | 3 Months<br>30° C.<br>65% Rh | Initial | 1 Month<br>30° C.<br>65% Rh | 3 Months<br>30° C.<br>65% Rh |
| Analysis of Pantoprazole Composition without Liquid Phase | | | | | | | |
| Description | | White colored powder | White colored powder | White colored powder | White colored powder | White colored powder | Brown colored crystal powder |
| Water content | | 0.489 | 0.555 | 0.537 | 0.571 | 0.553 | 6.350 |
| Assay - Pantoprazole | | 98.9 | 110.8 | 93.2 | 96.5 | 89.7 | 76.4 |
| RS | Imp A | 0.07 | 0.07 | 0.16 | 0.05 | 0.20 | 0.16 |
| | Imp B | ND | ND | ND | ND | ND | 0.18 |
| | Imp D&F | 0.05 | 0.11 | 0.41 | 0.06 | 0.14 | 1.43 |
| | Imp E | 0.01 | 0.02 | ND | 0.01 | ND | ND |
| | SMI | 0.03 | 0.03 | 0.08 | 0.02 | 0.02 | 0.33 |
| | Imp C | 0.01 | 0.00 | ND | 0.01 | 0.02 | 0.50 |
| | Total (Excluding Imp C) | 0.22 | 0.36 | 0.78 | 0.23 | 0.24 | 2.86 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.67 | 9.54 | 9.2 | 9.09 | 8.82 | 9.26 |
| Osmolality | | 273 | 290 | 280 | 281 | 288 | 280 |
| Assay - Pantoprazole | | NA | 94.8 | 95.8 | NA | 88.8 | 93.9 |
| Assay - NaCl | | 99.0 | 98.8 | 103.6 | 99.7 | 98.2 | 97.6 |
| RS | Imp A | NA | 0.07 | 0.08 | NA | NA | 0.07 |
| | Imp B | NA | ND | ND | NA | NA | ND |
| | Imp D&F | NA | 0.13 | 0.25 | NA | NA | 0.24 |
| | Imp E | NA | 0.01 | 0.02 | NA | NA | ND |
| | SMI | NA | 0.07 | 0.06 | NA | NA | 0.05 |
| | Imp C | NA | 0.03 | 0.06 | NA | NA | 0.12 |
| | Total (Excluding Imp C) | NA | 0.44 | 0.46 | NA | NA | 0.45 |
| LPC TEST 1A | 10 μm | NA | Complies | Complies | NA | Complies | Complies |
| | 25 μm | NA | | | NA | | |

TABLE 6C

Stability Testing at 30° C. and Relative Humidity of 65% of Pantoprazole
Compositions formed from Bulk Solutions Processed under Various Conditions (cont.)

|  |  | Exemplary Composition 17 | | | Exemplary Composition 18 | | |
|---|---|---|---|---|---|---|---|
| Bulk Solution Formulation | | IB | | | II | | |
| Blending Process | | Process I | | | Process II | | |
| Bulk Solution Temperature | | 4° C. with 0.45% NaCl | | | Water and Acetone | | |
| Condition | | Initial | 1 Month 30° C. 65% Rh | 3 Months 30° C. 65% Rh | Initial | 1 Month 30° C. 65% Rh | 3 Months 30° C. 65% Rh |
| Analysis of Pantoprazole Composition without Liquid Phase | | | | | | | |
| Description | | White colored powder | White colored powder | White colored powder | White colored powder | White colored powder | White colored powder |
| Water content | | 0.687 | 0.958 | 0.876 | NA | 0.698 | NA |
| Assay - Pantoprazole | | 97.2 | 89.6 | 94.4 | 100.4 | 99.5 | NA |
| RS | Imp A | 0.05 | 0.05 | 0.06 | 0.05 | 0.06 | NA |
|  | Imp B | ND | ND | ND | ND | ND | NA |
|  | Imp D&F | 0.06 | 0.18 | 0.24 | 0.02 | 0.05 | NA |
|  | Imp E | 0.01 | 0.02 | ND | 0.01 | 0.02 | NA |
|  | SMI | 0.02 | 0.06 | 0.03 | 0.02 | 0.02 | NA |
|  | Imp C | 0.01 | 0.03 | ND | ND | 0.01 | NA |
|  | Total (Excluding Imp C) | 0.19 | 0.48 | 0.41 | 0.16 | 0.19 | NA |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.62 | 9.13 | 9.17 | 9.36 | 9.39 | 9.32 |
| Osmolality | | 143 | 151 | 141 | 294 | 285 | 292 |
| Assay - Pantoprazole | | NA | 88.8 | 93.1 | 90.9 | 91.7 | 98 |
| Assay - NaCl | | 101.7 | 98.2 | 91 | NA | 98.4 | 99.6 |
| RS | Imp A | NA | NA | 0.06 | 0.06 | 0.05 | 0.05 |
|  | Imp B | NA | NA | NA | ND | ND | ND |
|  | Imp D&F | NA | NA | 0.22 | 0.03 | 0.08 | 0.12 |
|  | Imp E | NA | NA | NA | 0.01 | 0.02 | ND |
|  | SMI | NA | NA | 0.06 | 0.02 | 0.03 | 0.02 |
|  | Imp C | NA | NA | 0.06 | ND | 0.06 | 0.06 |
|  | Total (Excluding Imp C) | NA | NA | 0.39 | 0.21 | 0.25 | 0.21 |
| LPC TEST 1A | 10 μm | NA | Complies | Complies | Complies | Complies | NA |
|  | 25 μm | NA | | | | | NA |

TABLE 7A

Stability Testing at 40° C. and Relative Humidity of 15% of Pantoprazole
Compositions formed from Bulk Solutions Processed under Various Conditions

|  |  | Exemplary Composition 19 | | | Exemplary Composition 20 | | |
|---|---|---|---|---|---|---|---|
| Bulk Solution Formulation | | IA | | | IA | | |
| Blending Process | | Process I | | | Process I | | |
| Bulk Solution Temperature | | 25° C. | | | 25° C. | | |
| Condition | | Initial | 1 Month 40° C. 15% Rh | 3 Months 40° C. 15% Rh | Initial | 1 Month 40° C. 15% Rh | 3 Months 40° C. 15% Rh |
| Analysis of Pantoprazole Composition without Liquid Phase | | | | | | | |
| Description | | White colored powder | White colored powder | White colored powder | White colored powder | White colored powder | White colored powder |
| Water content | | 0.500 | 0.688 | 0.523 | 0.555 | 0.534 | 0.522 |
| Assay - Pantoprazole | | 99.2 | 96.4 | 93.9 | 99.2 | 98.5 | 88.4 |
| RS | Imp A | 0.07 | 0.07 | 0.08 | 0.07 | 0.07 | 0.10 |
|  | Imp B | ND | ND | ND | ND | ND | 0.02 |
|  | Imp D&F | 0.06 | 0.10 | 0.20 | 0.06 | 0.14 | 0.43 |
|  | Imp E | 0.01 | 0.01 | 0.01 | 0.01 | 0.01 | ND |

TABLE 7A-continued

Stability Testing at 40° C. and Relative Humidity of 15% of Pantoprazole
Compositions formed from Bulk Solutions Processed under Various Conditions

| Bulk Solution Formulation<br>Blending Process<br>Bulk Solution Temperature | | Exemplary Composition 19<br>IA<br>Process I<br>25° C. | | | Exemplary Composition 20<br>IA<br>Process I<br>25° C. | | |
|---|---|---|---|---|---|---|---|
| Condition | | Initial | 1 Month<br>40° C.<br>15% Rh | 3 Months<br>40° C.<br>15% Rh | Initial | 1 Month<br>40° C.<br>15% Rh | 3 Months<br>40° C.<br>15% Rh |
| | SMI | | 0.03 | 0.04 | 0.05 | 0.03 | 0.04 | 0.08 |
| | Imp C | | 0.01 | 0.00 | ND | 0.01 | 0.00 | ND |
| | Total (Excluding Imp C) | | 0.24 | 0.35 | 0.52 | 0.24 | 0.43 | 0.82 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.58 | 9.54 | 9.26 | 9.58 | 9.57 | 9.2 |
| Osmolality | | 279 | 294 | 275 | 273 | 286 | 278 |
| Assay - Pantoprazole | | Na | 91.9 | 99.8 | NA | 93.5 | 96 |
| Assay - NaCl | | 99.8 | 94.1 | 96.5 | 99.3 | 97.1 | 101.4 |
| RS | Imp A | NA | 0.04 | 0.09 | NA | 0.10 | 0.10 |
| | Imp B | NA | ND | 0.02 | NA | ND | 0.03 |
| | Imp D&F | NA | 0.10 | 0.40 | NA | 0.28 | 0.51 |
| | Imp E | NA | ND | NA | NA | 0.01 | NA |
| | SMI | NA | 0.05 | 0.09 | NA | 0.08 | 0.11 |
| | Imp C | NA | 0.02 | NA | NA | 0.06 | 0.04 |
| | Total (Excluding Imp C) | NA | 0.27 | 0.73 | NA | 0.73 | 0.94 |
| LPC TEST 1A | 10 μm | NA | Complies | NA | NA | Complies | Complies |
| | 25 μm | NA | | NA | NA | | |

TABLE 7B

Stability Testing at 40° C. and Relative Humidity of 15% of Pantoprazole
Compositions formed from Bulk Solutions Processed under Various Conditions (cont.)

| Bulk Solution Formulation<br>Blending Process<br>Bulk Solution Temperature | | Exemplary Composition 21<br>IA<br>Process I<br>4° C. | | | Exemplary Composition 22<br>IA<br>Process I<br>4° C., Exposed to 30/65 for 7.30 hr | | |
|---|---|---|---|---|---|---|---|
| Condition | | Initial | 1 Month<br>40° C.<br>15% Rh | 3 Months<br>40° C.<br>15% Rh | Initial | 1 Month<br>40° C.<br>15% Rh | 3 Months<br>40° C.<br>15% Rh |
| Analysis of Pantoprazole Composition without Liquid Phase | | | | | | | |
| Description | | White colored powder | White colored powder | White colored powder | White colored powder | White colored powder | Off White Powder |
| Water content | | 0.489 | 0.569 | 0.623 | 0.571 | 0.507 | 0.506 |
| Assay - Pantoprazole | | 98.9 | 96.7 | 90.6 | 96.5 | 85.9 | 87.0 |
| RS | Imp A | 0.07 | 0.07 | 0.22 | 0.05 | 0.04 | 0.22 |
| | Imp B | ND | ND | 0.04 | ND | ND | 0.14 |
| | Imp D&F | 0.05 | 0.15 | 0.98 | 0.06 | 0.31 | 2.21 |
| | Imp E | 0.01 | 0.01 | ND | 0.01 | 0.01 | ND |
| | SMI | 0.03 | 0.04 | 0.13 | 0.02 | 0.05 | 0.32 |
| | Imp C | 0.01 | 0.00 | ND | 0.01 | 0.08 | 0.96 |
| | Total (Excluding Imp C) | 0.22 | 0.44 | 1.71 | 0.23 | 0.65 | 3.42 |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Clear Colorless Solution |
| pH | | 9.67 | 9.53 | 9.19 | 9.09 | 8.8 | 9.07 |
| Osmolality | | 273 | 289 | 279 | 281 | 289 | 274 |
| Assay - Pantoprazole | | NA | 92.6 | 96.3 | NA | 89.6 | 86.1 |

TABLE 7B-continued

Stability Testing at 40° C. and Relative Humidity of 15% of Pantoprazole
Compositions formed from Bulk Solutions Processed under Various Conditions (cont.)

| Bulk Solution Formulation<br>Blending Process<br>Bulk Solution Temperature | | Exemplary Composition 21<br>IA<br>Process I<br>4° C. | | | Exemplary Composition 22<br>IA<br>Process I<br>4° C., Exposed to 30/65 for 7.30 hr | | |
|---|---|---|---|---|---|---|---|
| Condition | | Initial | 1 Month<br>40° C.<br>15% Rh | 3 Months<br>40° C.<br>15% Rh | Initial | 1 Month<br>40° C.<br>15% Rh | 3 Months<br>40° C.<br>15% Rh |
| Assay - NaCl | | | 99.0 | 98.0 | 103.8 | 99.7 | 98.4 | 99.1 |
| RS | Imp A | NA | 0.08 | 0.06 | NA | NA | 0.06 |
| | Imp B | NA | ND | 0.01 | NA | NA | 0.04 |
| | Imp D&F | NA | 0.23 | 0.31 | NA | NA | 0.68 |
| | Imp E | NA | 0.02 | NA | NA | NA | NA |
| | SMI | NA | 0.09 | 0.06 | NA | NA | 0.43 |
| | Imp C | NA | 0.04 | 0.02 | NA | NA | 1.25 |
| | Total (Excluding Imp C) | NA | 0.61 | 0.60 | NA | NA | 2.02 |
| LPC TEST 1A | 10 μm | NA | Complies | Complies | NA | Complies | Complies |
| | 25 μm | NA | | | NA | | |

TABLE 7C

Stability Testing at 40° C. and Relative Humidity of 15% of Pantoprazole
Compositions formed from Bulk Solutions Processed under Various Conditions (cont.)

| Bulk Solution Formulation<br>Blending Process<br>Bulk Solution Temperature | | Exemplary Composition 23<br>IB<br>Process I<br>4° C., with 0.45% NaCl | | | Exemplary Composition 24<br>II<br>Process II<br>Water and Acetone | | |
|---|---|---|---|---|---|---|---|
| Condition | | Initial | 1 Month<br>40° C.<br>15% Rh | 3 Months<br>40° C.<br>15% Rh | Initial | 1 Month<br>40° C.<br>15% Rh | 3 Months<br>40° C.<br>15% Rh |
| Analysis of Pantoprazole Composition without Liquid Phase | | | | | | | |
| Description | | White colored powder | White colored powder | White colored powder | White colored powder | White colored powder | Off-White Colored powder |
| Water content | | 0.687 | 0.858 | 0.845 | NA | 0.788 | NA |
| Assay - Pantoprazole | | 97.2 | 86.3 | 91.7 | 100.4 | 98.5 | NA |
| RS | Imp A | 0.05 | 0.05 | 0.09 | 0.05 | 0.07 | NA |
| | Imp B | ND | ND | 0.01 | ND | ND | NA |
| | Imp D&F | 0.06 | 0.16 | 0.49 | 0.02 | 0.25 | NA |
| | Imp E | 0.01 | 0.02 | ND | 0.01 | 0.02 | NA |
| | SMI | 0.02 | 0.03 | 0.05 | 0.02 | 0.04 | NA |
| | Imp C | 0.01 | 0.02 | 0.04 | ND | 0.01 | NA |
| | Total (Excluding Imp C) | 0.19 | 0.37 | 0.79 | 0.16 | 0.52 | NA |
| Analysis of Pantoprazole Composition combined with Liquid Phase | | | | | | | |
| Description | | Clear Colorless Solution | Clear Colorless Solution | Clear Colorless Solution | Clear Colorless Solution | Clear Colorless Solution | Yellowish Clear Solution |
| pH | | 9.62 | 9.17 | 9.11 | 9.36 | 9.41 | 9.39 |
| Osmolality | | 143 | 148 | 428 | 294 | 291 | 286 |
| Assay - Pantoprazole | | NA | 89.4 | 95.1 | 90.9 | 92.5 | 95.2 |
| Assay - NaCl | | 101.7 | 99.5 | 296 | NA | 98.6 | 101.2 |
| RS | Imp A | NA | NA | 0.09 | 0.06 | 0.08 | 0.16 |
| | Imp B | NA | NA | NA | ND | ND | 0.05 |
| | Imp D&F | NA | NA | 0.51 | 0.03 | 0.40 | 0.89 |
| | Imp E | NA | NA | NA | 0.01 | 0.01 | 0.01 |
| | SMI | NA | NA | 0.07 | 0.02 | 0.05 | 0.08 |
| | Imp C | NA | NA | 0.11 | ND | 0.23 | 0.51 |
| | Total (Excluding Imp C) | NA | NA | 0.91 | 0.21 | 0.77 | 1.62 |
| LPC TEST 1A | 10 μm | NA | Complies | Complies | Complies | Complies | NA |
| | 25 μm | NA | | | | | NA |

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A spray-dried storage stable pantoprazole composition comprising:
   pantoprazole; and
   an excipient matrix comprising sodium chloride (NaCl), wherein the sodium chloride and the pantoprazole are present at a weight ratio of between 50:1 and 5:1;
   wherein the pantoprazole is substantially uniformly dispersed in the excipient matrix; and
   wherein the pantoprazole composition is storage stable such that, after storage at 25° C. and 40% relative humidity for 12 weeks, the composition contains equal or less than 0.20% by weight of a pantoprazole sulfone degradant (Impurity-A) and equal or less than 0.20% by weight of a pantoprazole Methyl degradant (Impurity-D&F).

2. The storage stable pantoprazole composition of claim 1, wherein the pantoprazole is in form of pantoprazole sodium sesquihydrate.

3. The storage stable pantoprazole composition of claim 1, wherein the pantoprazole and the sodium chloride are present in a weight ratio of about 1:11 or about 1:22.

4. The storage stable pantoprazole composition of claim 1, wherein the excipient further comprises a compound selected from the group consisting of a salt other than sodium chloride, an amino acid, and a sugar.

5. The storage stable pantoprazole composition of claim 1, wherein the composition, after storage at 25° C. and 40% relative humidity for 12 weeks, contains equal or less than 0.1% by weight of a pantoprazole sulfone degradant based on a total weight of the composition.

6. A kit comprising:
   a. a storage stable pantoprazole composition according to claim 1;
   b. a liquid phase; and
   c. a container that separately contains the pantoprazole composition and the liquid phase.

7. The kit of claim 6, wherein the container comprises a first pouch and wherein the storage stable pantoprazole composition is contained in a first chamber of the first pouch comprising a polymeric material.

8. The kit of claim 7, wherein the container comprises a second pouch and wherein the liquid phase is contained is contained in a second chamber of the second pouch comprising a polymeric material, wherein the first pouch and the second pouch are coupled together, and wherein the first chamber and the second chamber are fluidly isolated from each other.

9. The kit of claim 6, wherein the storage stable pantoprazole composition is present in an amount of from about 20 to about 100 mg.

10. The kit of claim 6, wherein the liquid phase comprises water.

11. The kit of claim 6, wherein the liquid phase is present in an amount of from about 10 to about 200 mL.

12. A method for forming a storage stable pantoprazole composition, comprising:
  combining a bulking agent and water to form a first solution;
  combining pantoprazole and the first solution to form a second solution;
  combining sodium hydroxide and the second solution to form a bulk solution; and
  removing water from the bulk solution by a spray-dry process to form the storage stable pantoprazole composition;
  wherein the bulking agent and the pantoprazole are present in the storage stable pantoprazole composition at a weight ratio of between 50:1 and 5:1; and
  wherein the pantoprazole composition is storage stable such that, after storage at 25° C. and 40% relative humidity for 12 weeks, the composition contains equal or less than 0.20% by weight of a pantoprazole sulfone degradant (Impurity-A) and equal or less than 0.20% by weight of a pantoprazole Methyl degradant (Impurity-D&F).

13. The method of claim 12, wherein the spray dry process is selected from the group consisting of spray-drying, spray solidification, and spray pilling.

14. The method of claim 12, wherein the bulking agent comprises a compound selected from the group consisting of a salt, an amino acid, and a sugar.

15. The method of claim 14, wherein:
  a. the salt is selected from the group consisting of sodium chloride (NaCl), magnesium chloride (MgCl2), and calcium chloride (CaCl2);
  b. the amino acid comprises glycine;
  c. the sugar comprises dextrose, sucrose, trehalose, or combinations thereof; or
  d. any combination of a. through c.

16. The method of claim 12, wherein the sodium hydroxide is combined with the second solution in an amount sufficient for the bulk solution to have a pH of from about 8 to about 10.

17. The method of claim 12, wherein the step of combining the sodium hydroxide and the second solution is further defined as forming a third solution, and wherein the method further comprises combining a solvent and the third solution to form the bulk solution.

18. The method of claim 17, wherein the solvent comprises acetone.

19. The method of claim 12, wherein the water combined with the bulking agent has a temperature of from about 1° C. to about 10° C.

20. The method of claim 12, wherein the water combined with the bulking agent has a temperature of from about 15° C. to about 30° C.

* * * * *